US012577185B2

(12) United States Patent
Prakash et al.

(10) Patent No.: US 12,577,185 B2
(45) Date of Patent: Mar. 17, 2026

(54) SOLVENT DRYING SOLUTION AND PROCESSES THERFOR

(71) Applicant: Aquafortus Technologies Limited, Auckland (NZ)

(72) Inventors: Chaitra Prakash, Auckland (NZ); Haiming Tang, Auckland (NZ); Crystal Maddox, Auckland (NZ)

(73) Assignee: Aquafortus Technologies Limited, Auckland (NZ)

( * ) Notice: Subject to any disclaimer, the term of this patent is extended or adjusted under 35 U.S.C. 154(b) by 445 days.

(21) Appl. No.: 18/013,852

(22) PCT Filed: Jul. 9, 2021

(86) PCT No.: PCT/NZ2021/050106
§ 371 (c)(1),
(2) Date: Dec. 29, 2022

(87) PCT Pub. No.: WO2022/010367
PCT Pub. Date: Jan. 13, 2022

(65) Prior Publication Data
US 2024/0262772 A1 Aug. 8, 2024

Related U.S. Application Data

(60) Provisional application No. 63/084,856, filed on Sep. 29, 2020, provisional application No. 63/050,546, filed on Jul. 10, 2020.

(51) Int. Cl.
*C07C 29/86* (2006.01)
*B01D 11/04* (2006.01)
(Continued)

(52) U.S. Cl.
CPC .......... *C07C 29/86* (2013.01); *B01D 11/0488* (2013.01); *B01D 11/0492* (2013.01);
(Continued)

(58) Field of Classification Search
CPC ......... C07C 29/86; C07C 45/90; C07C 67/58; C07C 209/86; C07C 213/10;
(Continued)

(56) References Cited

U.S. PATENT DOCUMENTS 2,784,173 A 3/1957 Carmack
3,077,500 A 2/1963 Heinz et al.
(Continued)

FOREIGN PATENT DOCUMENTS

AU 2018 346 086 A1 5/2020
CA 1208134 A 7/1986
(Continued)

OTHER PUBLICATIONS

U.S. Appl. No. 17/436,439, filed Sep. 3, 2021, Daryl Joseph Briggs, US 20220185754.
(Continued)

*Primary Examiner* — Joseph W Drodge
(74) *Attorney, Agent, or Firm* — Nelson Mullins Riley & Scarborough LLP; Jane E. Remillard, Esq.; Jill Gorny Sloper, Esq.

(57) ABSTRACT

The present disclosure relates to a solvent drying solution and processes therefor. The present disclosure more specifically relates to a solvent drying solution that in use releases water from a solvent mixture. The present disclosure also relates to a process for recovering a solvent drying solution, more specifically to a process for recovering a solvent drying solution by using an osmotic process.

24 Claims, 7 Drawing Sheets

(51) Int. Cl.

| | |
|---|---|
| ***B01D 61/02*** | (2006.01) |
| ***C02F 1/44*** | (2023.01) |
| ***C07C 45/90*** | (2006.01) |
| ***C07C 67/58*** | (2006.01) |
| ***C07C 209/86*** | (2006.01) |
| ***C07C 213/10*** | (2006.01) |
| ***C07C 227/40*** | (2006.01) |
| ***C07C 231/24*** | (2006.01) |
| ***C07D 307/08*** | (2006.01) |

(52) U.S. Cl.
CPC ............ *B01D 61/025* (2013.01); *C02F 1/441* (2013.01); *C07C 45/90* (2013.01); *C07C 67/58* (2013.01); *C07C 209/86* (2013.01); *C07C 213/10* (2013.01); *C07C 227/40* (2013.01); *C07C 231/24* (2013.01); *C07D 307/08* (2013.01)

(58) Field of Classification Search
CPC . C07C 227/40; C07C 231/24; B01D 11/0488; B01D 11/0492; B01D 61/025; B01D 12/00; B01D 17/00; B01D 17/02; B01D 17/0202; C02F 1/441; C02F 1/445; C02F 1/447; C02F 1/448; C02F 2101/345; C07D 307/08
See application file for complete search history.

(56) References Cited

U.S. PATENT DOCUMENTS

| | | | | |
|---|---|---|---|---|
| 3,130,156 | A | 4/1964 | Neff | |
| 3,164,539 | A | 1/1965 | Smith | |
| 3,641,181 | A * | 2/1972 | Robbins | C07C 7/00 585/866 |
| 3,962,074 | A | 6/1976 | Schropp | |
| 4,275,234 | A | 6/1981 | Baniel et al. | |
| 4,624,958 | A | 11/1986 | Glazer | |
| 4,789,482 | A | 12/1988 | DiLeo et al. | |
| 5,186,817 | A * | 2/1993 | Paspek | C02F 1/26 210/708 |
| 5,346,620 | A | 9/1994 | Hendrix et al. | |
| 5,486,314 | A | 1/1996 | Wack et al. | |
| 5,705,074 | A | 1/1998 | Brient | |
| 5,780,276 | A | 7/1998 | Baniel | |
| 5,897,750 | A | 4/1999 | Berg | |
| 6,307,087 | B1 | 10/2001 | Buchwald et al. | |
| 6,858,694 | B2 | 2/2005 | Ohnishi et al. | |
| 6,858,964 | B2 | 2/2005 | Masumoto et al. | |
| 7,560,029 | B2 | 7/2009 | Mc Ginnis | |
| 8,143,444 | B2 | 3/2012 | Mariansky et al. | |
| 9,630,861 | B2 | 4/2017 | Ikeda et al. | |
| 10,933,377 | B2 | 3/2021 | Briggs et al. | |
| 11,020,706 | B2 | 6/2021 | Briggs | |
| 11,826,704 | B2 | 11/2023 | Briggs | |
| 11,987,506 | B2 | 5/2024 | Briggs et al. | |
| 2002/0156295 | A1 | 10/2002 | Buchwald et al. | |
| 2003/0004202 | A1 | 1/2003 | Elliott et al. | |
| 2006/0086664 | A1 * | 4/2006 | Wills | C12C 11/11 210/770 |
| 2012/0043274 | A1 | 2/2012 | Chi et al. | |
| 2012/0241377 | A1 | 9/2012 | Ooi et al. | |
| 2013/0012738 | A1 * | 1/2013 | Wu | B01D 11/0426 562/608 |
| 2013/0240444 | A1 | 9/2013 | Jung et al. | |
| 2014/0076810 | A1 | 3/2014 | Jessop et al. | |
| 2014/0158621 | A1 | 6/2014 | Lee et al. | |
| 2014/0290854 | A1 | 10/2014 | Parellada Llobet et al. | |
| 2014/0319056 | A1 | 10/2014 | Fuchigami et al. | |
| 2015/0108061 | A1 | 4/2015 | Chi et al. | |
| 2015/0166363 | A1 | 6/2015 | Eyal et al. | |
| 2015/0273396 | A1 | 10/2015 | Hancock et al. | |
| 2015/0360973 | A1 | 12/2015 | Eyal et al. | |
| 2016/0023171 | A1 | 1/2016 | Phillip et al. | |
| 2016/0158705 | A1 | 6/2016 | Helm et al. | |
| 2016/0175777 | A1 | 6/2016 | Ikeda et al. | |
| 2017/0305823 | A1 | 10/2017 | Fischer et al. | |
| 2017/0354904 | A1 | 12/2017 | Wilson et al. | |
| 2018/0008933 | A1 | 1/2018 | Hu et al. | |
| 2018/0015414 | A1 | 1/2018 | Hu et al. | |
| 2018/0142117 | A1 | 5/2018 | Resendes et al. | |
| 2019/0099718 | A1 | 4/2019 | Briggs et al. | |
| 2020/0023316 | A1 | 1/2020 | Briggs | |
| 2020/0308023 | A1 | 10/2020 | Briggs et al. | |
| 2022/0185754 | A1 | 6/2022 | Briggs et al. | |
| 2022/0193608 | A1 | 6/2022 | Briggs | |
| 2023/0043356 | A1 | 2/2023 | Prakash et al. | |
| 2023/0257284 | A1 | 8/2023 | Briggs et al. | |
| 2023/0286833 | A1 | 9/2023 | Prakash et al. | |
| 2024/0262772 | A1 | 8/2024 | Prakash et al. | |
| 2024/0368001 | A1 | 11/2024 | Briggs et al. | |

FOREIGN PATENT DOCUMENTS

| | | | | |
|---|---|---|---|---|
| CN | 1156418 | A | 8/1997 | |
| CN | 1717386 | A | 1/2006 | |
| CN | 104619649 | A | 5/2015 | |
| CN | 104984562 | A | 10/2015 | |
| CN | 106727143 | A | 5/2017 | |
| CN | 106942264 | A | 7/2017 | |
| CN | 108186380 | A | 6/2018 | |
| CN | 110099869 | A | 8/2019 | |
| DE | 10 2018 119168 | A1 | 2/2019 | |
| EP | 0117870 | A1 | 9/1984 | |
| EP | 1236751 | A1 | 9/2002 | |
| JP | S5610131 | A | 2/1981 | |
| JP | H02-49195 | A | 2/1990 | |
| JP | H04266845 | A | 9/1992 | |
| JP | 2007-511472 | A | 5/2007 | |
| JP | 2009200349 | A | 9/2009 | |
| JP | 2013 518718 | A | 5/2013 | |
| WO | 2004050601 | A2 | 6/2004 | |
| WO | 2011/014850 | A2 | 2/2011 | |
| WO | 2011/028629 | A1 | 3/2011 | |
| WO | 2013/016491 | A1 | 1/2013 | |
| WO | 2013/016499 | A1 | 1/2013 | |
| WO | 2013175380 | A1 | 11/2013 | |
| WO | 2014089142 | A1 | 6/2014 | |
| WO | 2014191504 | A1 | 12/2014 | |
| WO | 2014191522 | A1 | 12/2014 | |
| WO | 2016094835 | A1 | 6/2016 | |
| WO | 2016133464 | A1 | 8/2016 | |
| WO | WO-2018067019 | A2 * | 4/2018 | C07C 49/08 |
| WO | 2019/070134 | A2 | 4/2019 | |
| WO | 2020/204733 | A1 | 10/2020 | |
| WO | 2022/010366 | A1 | 1/2022 | |
| WO | 2022/010367 | A1 | 1/2022 | |

OTHER PUBLICATIONS

U.S. Appl. No. 17/246,440, filed Apr. 30, 2021, Daryl Joseph Briggs, U.S. Pat. No. 11,826,704.
U.S. Appl. No. 16/338,076, filed Mar. 29, 2019, Daryl Joseph Briggs, U.S. Pat. No. 11,020,706.
U.S. Appl. No. 17/599,284, filed Sep. 28, 2021, Chaitra Prakash, US 20230043356.
U.S. Appl. No. 16/753,263, filed Apr. 2, 2020, Daryl Joseph Briggs, US 20200308023.
U.S. Appl. No. 18/093,263, filed Jan. 4, 2023, Daryl Joseph Briggs, US 20230257284.
U.S. Appl. No. 16/145,968, filed Sep. 28, 2018, Daryl Joseph Briggs, U.S. Pat. No. 10,933,377.
U.S. Appl. No. 18/013,853, filed Dec. 29, 2022, Chaitra Prakash, US 20230286833.
Extended European Search Report, European Application No. 21837257.1, dated Apr. 3, 2024, 8 pages.
Deshpande, M., "Polyol induced extraction (PIE) of water from organic solvents,"), Seton Hall University Dissertations and Theses (ETDs). No. 1989. (2014) Retrieved from the Internet on Sep. 21, 2021 via <URL:https://scholarship.shu.edu/dissertations/1989/- retrieved on Sep. 21, 2021.

(56) References Cited

OTHER PUBLICATIONS

International Search Report and Written Opinion, PCT/NZ2021/050106, dated Oct. 5, 2021, 21 pages.
International Preliminary Report on Patentability, PCT/NZ2021/050106, dated Jan. 10, 2023, 13 pages.
Alonso, I. , et al., "Thermodynamics of Ketone + Amine Mixtures. Part III. Volumetric and Speed of Sound Data at (293.15, 298.15, and 303.15) K for 2-Butanone + Aniline, + N-Methylaniline, or + Pyridine Systems," J. Chem. Eng. Data, vol. 55: 5400-5405 (2010).
Bahadur Alisha, S. et al., "Ultrasonic Studies on Binary Liquid Mixtures of Triethylamine with Carbitols at 308.15 K," Indian Journal of Advances in Chemical Science, vol. 5(3): 148-154 (2017).
CAS Registry No. 183205-66-5; STN Entry date Nov. 20, 1996; Ethanesulfonic acid, 2-hydroxy-compd with N, N-diethylethanamine (1:1), 1 page, Retrieved on May 18, 2020.
Extended European Search Report, European Application No. 20768998, dated Nov. 4, 2022, 9 pages.
González, J-A., et al. "Thermodynamics of ketone + amine mixtures. Part X. Excess molar enthalpies at 298.15 K for N,N, N-triethylamine + 2-alkanone systems. Characterization of tertiary amine + 2-alkanone, and of amino-ketone + n-alkane mixtures in terms of DISQUAC," Fluid Phase Equilibria, vol. 356: 117-125 (2013).
Govindarajan, M. et al., "Salt effect on liquid-liquid equilibrium of the methyl isobutyl ketone-acetic acid-water system at 35° C.," Fluid Phase Equilibria, vol. 108: 269-292 (1995).
Guo, C. et al., Structural Characteristic Integrated Computer-Aided Molecular Design for Phenols Removal Considering Synergistic Effect, Industrial & Engineering Chemistry Research, vol. 57:11374-11380 (2018).
Gutierrez, E. et al., "Phase segregation in aqueous solutions of non-ionic surfactants using ammonium, magnesium and iron salts", The Journal of Chemical Thermodynamics, vol. 70: 147-153 (2014).
Hyde, A.M., et al., "General Principles and Strategies for Salting-Out Informed by the Hofmeister Series," Organic Process Research and Development, vol. 21:1335-1370 (2017).
International Preliminary Report on Patentability, PCT/NZ2017/050127, dated Apr. 9, 2019, 6 pages.
International Preliminary Report on Patentability, PCT/NZ2018/050135, dated Apr. 8, 2020, 8 pages.
International Preliminary Report on Patentability, PCT/NZ2020/050019, dated Aug. 25, 2021, 4 pages.
International Preliminary Report on Patentability, PCT/NZ2021/050105, dated Jan. 10, 2023, 8 pages.
International Search Report and Written Opinion, PCT/NZ2017/050127, dated Jan. 22, 2019, 8 pages.
International Search Report and Written Opinion, PCT/NZ2018/050135, dated Nov. 14, 2019, 11 pages.
International Search Report and Written Opinion, PCT/NZ2020/050019, dated Jun. 10, 2020, 7 pages.
International Search Report and Written Opinion, PCT/NZ2021/050105, dated Oct. 5, 2021, 11 pages.
Li, H-B. et al., Preparative isolation and purification of salidroside from the Chinese medicinal plant Rhodiola sachalinensis by high-speed counter-current chromatography, Journal of Chromatography A,, vol. 932: 91-95 (2001).
Matkovich, C.E. et al., "Salting-Out of Acetone from Water—Basis of a New Solvent Extraction System," Analytical Chemistry, vol. 45(11): 1915-1921 (1973).
Munson, C. L. et al. "Factors influencing Solvent Selection for Extraction of Ethanol from Aqueous Solutions," Ind. Eng. Chem. Process Des. Dev., vol. 23 (1):109-115 (1984).
Reddy, K.C. et al., "Ultrasonic Behaviour of Binary Liquid Mixtures Containing Trie thy lamine, Part 1," Trans. Faraday Soc., vol. 58: 2352-2357 (1962).
Walsham, J. G., "Prediction of Flash Points for Solvent Mixtures" Advances in Chemistry, vol. 124, chapter 5: 56-69 (1973).

* cited by examiner

SOLVENT DRYING SOLUTION AND PROCESSES THERFOR

CROSS-REFERENCE TO RELATED APPLICATIONS

This application is a 35 U.S.C. § 371 national stage filing of International Application No. PCT/NZ2021/050106, filed Jul. 9, 2021, which claims priority to U.S. Provisional Application No. 63/050,546, filed Jul. 10, 2020, and U.S. Provisional Application No. 63/084,856, filed Sep. 29, 2020. The contents of the aforementioned applications are hereby incorporated by reference in their entirety.

FIELD OF THE INVENTION

The present disclosure relates to a solvent drying solution and processes therefor. The present disclosure more specifically relates to a solvent drying solution that in use releases water from a solvent mixture. The present disclosure also relates to a process for recovering a solvent drying solution, more specifically to a process for recovering a solvent drying solution used in an osmotic process.

BACKGROUND OF THE INVENTION

A salt recovery solvent solution has been developed by the applicant and disclosed in co-pending U.S. Provisional Application No. 63/050,402 filed Jul. 10, 2020, the entire contents of which are incorporated herein by reference.

The extraction of water or drying of water from solvent mixtures is typically a high energy and time-consuming task.

Jessop et. al. in US 2014/0076810 describe a reversible water or aqueous solution and its use. The reversible water or aqueous solution is formed by adding an ionisable additive comprising an ionisable functional group having at least one nitrogen atom. The additive is further described as a monoamine, a diamine, a triamine, a tetramine or a polyamine, such as a polymer or a biopolymer. The reversible water or aqueous solution is capable of reversibly switching between an initial ionic strength and an increased ionic strength by using a trigger, such as bubbling with $CO_2$, $CS_2$ or COS or treatment with a Bronsted acid such as formic acid, hydrochloric acid, sulphuric acid or carbonic acid. To enable this reversibility the ionic form of the additive should be capable of deprotonation through the action of the ionising trigger. This necessarily requires a reversible interaction between the ionic form of the trigger and the additive as shown in FIG. 1 of Jessop. The reversibility of the water or aqueous solution allows for the control of solubility or insolubility of various hydrophobic liquids or solvents in the water or aqueous solution. This provides a means of separating moderately hydrophobic solvents from the switchable water. However, one of the difficulties with the Jessop work is that is difficult to disassociate the $CO_2$ from the amine to achieve the reversible water. Trace amounts of $CO_2$ and amine can remain solubilised in the draw solution and heating, stripping and the kinetics of recovery are slow, energy intensive in the of the order of hours to minutes.

It is an object of the present invention to provide a solvent drying solution that overcomes these difficulties or to at least provide a useful alternative.

SUMMARY OF THE INVENTION

In a first aspect, the present invention provides a solvent drying solution, the solution comprising:

a) at least one $C_1$-$C_7$ alkylamine or quaternary ammonium containing compound; or b) at least one carboxylic acid containing compound or an alkylsulfonic acid; or c) at least one straight chain or branched $C_3$-$C_9$ alkyl substituted by —OH; or d) a combination of a) to c) thereof, in a water containing solvent comprising at least two or more components independently selected from any combination of integers i), ii), iii) and iv), where i) is a straight, branched or optionally substituted cyclic $C_4$-$C_9$ ether containing compound;

ii) is a straight chain or branched $C_3$-$C_9$ alkyl substituted by —OH;

iii) is a straight chain, branched or cyclic $C_4$-$C_9$ ketone or $C_4$-$C_9$ diketone; and iv) is a straight chain or branched $C_3$-$C_9$ ester containing compound;

wherein at least one component of the water containing solvent is substantially immiscible with an aqueous solution of 1 molar sodium chloride at or above 20 degrees Celsius and at 1 atmosphere.

In one embodiment the water containing solvent comprises an amine containing compound as a substitute to one of integers i), ii), iii) and iv).

In one embodiment the carboxylic acid containing compound is selected from one or more of the following:

a) a compound of Formula I,

Formula I

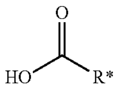

wherein R* is selected from, —$C_1$-$C_7$ alkyl-OH, —$C_1$-$C_7$ alkyl, —$C_1$-$C_7$ alkyl-$NH_2$, —$C_1$-$C_7$ alkyl-$NHR_3$ and —$C_1$-$C_7$ alkyl $NR_3R_4$, wherein each $R_3$ and $R_4$ are selected from —H, —OH, -halo, —$C_1$-$C_7$ alkyl, —$C_1$-$C_7$ alkyl-OH, —C(O)OH, —C(O)—H, or —C(O)—($C_1$-$C_7$ alkyl); and b) a polymer containing one or more carboxylic acid groups.

In one embodiment the alkylsulfonic acid is isoethionic acid.

In one embodiment the solvent drying solution comprises at least one $C_1$-$C_7$ alkyl amine or quaternary ammonium containing compound.

In one embodiment the at least one $C_1$-$C_7$ alkyl amine or quaternary ammonium containing compound of the solvent drying solution is selected from one or more of betaine, carnitine, urea and choline. In one embodiment each of betaine, carnitine, urea and choline may optionally include a counterion or a zwitterion. In one embodiment the counterion may be selected without limitation from a carboxylic acid, such as citrate, glycolate or chloride. In one embodiment the zwitterion may be selected from trimethyl glycine, L-carnitine or [2(methacryloxyl)ethyl]dimethyl-(3-sulfopropyl) ammonium hydroxide.

In one embodiment the solvent drying solution comprises at least one straight chain or branched $C_3$-$C_9$ alkyl substituted by —OH.

In one embodiment the at least one straight chain or branched $C_3$-$C_9$ alkyl substituted by —OH of the solvent drying solution includes at least two —OH substituents.

In one embodiment the at least one straight chain or branched $C_3$-$C_9$ alkyl substituted by —OH of the solvent drying solution is selected from 1,4 butanediol, glycerol or combinations thereof.

In one embodiment the solvent drying solution comprises at least one carboxylic acid containing compound.

In one embodiment the solvent drying solution comprises betaine.

In one embodiment the solvent drying solution comprises sarcosine.

In one embodiment the solvent drying solution comprises choline chloride.

In one embodiment the solvent drying solution comprises a combination of betaine and sarcosine. In one embodiment the molar ratio of betaine to sarcosine is about 2:1.

In one embodiment the solvent drying solution comprises a combination of choline chloride and 1,4-butanediol. In one embodiment the molar ratio of choline chloride to 1,4-butanediol is about 1:2.

In one embodiment the solvent drying solution comprises a combination of choline chloride and glycerol. In one embodiment the molar ratio of choline chloride to glycerol is about 1:2.

In one embodiment the solvent drying solution comprises a combination of choline chloride and sarcosine. In one embodiment the molar ratio of choline chloride to sarcosine is about 1:2.

In one embodiment the solvent drying solution comprises a combination of choline chloride and urea. In one embodiment the molar ratio of choline chloride to urea is about 1:2.

In one embodiment the $C_4$-$C_9$ ether containing compound is selected from one or more of 2-methyltetrahydrofuran, 3-methyltetrahydrofuran, 2-ethyltetrahydrofuran, 3-ethyltetrahydrofuran, dioxane, 1-ethoxypropane, and a $C_4$-$C_9$ glycol ether or combinations thereof.

In one embodiment the straight chain or branched $C_3$-$C_9$ alkyl substituted by —OH is selected from one or more of 1-butanol, 2, butanol and 1-pentanol or combinations thereof.

In one embodiment the $C_4$-$C_9$ glycol ether is selected from one or more of propylene glycol methyl ether, dipropylene glycol methyl ethyl actetate, dipropylene glycol n-propyl ether, propylene glycol n-butyl ether, dipropylene glycol n-butyl ether, tripropylene glycol n-butyl ether, propylene glycol phenyl ether, propylene glycol diacetate or combinations thereof.

In one embodiment the $C_4$-$C_9$ ketone or diketone is selected from one or more of acetonylacetone or 2-butanone.

In one embodiment the $C_3$-$C_9$ ester is methyl acetate, or ethyl acetate.

In one embodiment the amine containing compound is a secondary or tertiary amine containing compound or a combination thereof.

In one embodiment the amine containing compound is triethylamine.

In one embodiment the solvent is a combination of 2-methyltetrahydrofuran and acetonylacetone.

In one embodiment the solvent is a combination of 2-methyltetrahydrofuran and 1-butanol.

In one embodiment the solvent is a combination of 2-methyltetrahydrofuran and 1-pentanol.

In one embodiment the solvent is a combination of ethyl acetate and 2-butanone.

In one embodiment the solvent is a combination of ethyl acetate and 2-methyltetrahydrofuran.

In one embodiment the solvent is a combination of ethyl acetate and 1-butanol.

In one embodiment the solvent is a combination of ethyl acetate and acetonylacetone.

In one embodiment the solvent is a combination of ethyl acetate and 2-butanone.

In one embodiment the solvent is a combination of triethylamine and 2-butanone.

In a second aspect, the present invention provides a method of recovering water from a solvent drying solution, the method including the steps of contacting the water containing solvent as defined above with:

a) at least one $C_1$-$C_7$ alkyl amine or quaternary ammonium containing compound and
b) at least one carboxylic acid containing compound, or an alkylsulfonic acid;
c) at least one at least one straight chain or branched $C_3$-$C_9$ alkyl substituted by —OH; or
d) a combination of a) to c) thereof, where upon contact the water is released from the water containing solvent, the water released forming an aqueous layer with the immiscible water depleted solvent layer.

In one embodiment the method is included in a counter current process.

In one embodiment the method includes the step of separating the recovered water from the immiscible water depleted solvent layer.

In one embodiment the process includes the step of recovering the solvent.

In one embodiment the recovered solvent drying solution is recycled for use in a further solvent drying process. In a preferred embodiment the process of recovering the solvent drying solution is a continuous recovery process.

In one embodiment the step of recovering the solvent drying solution is achieved by one or more of the following techniques, membrane distillation, pervaporation, osmosis, pressure driven membrane processes, osmotically driven membrane processes, osmotically assisted pressure driven membrane processes, pressure assisted osmotically driven membrane processes, filtration, mechanical vapor recompression, evaporation based processes, water specific reactant, or crystallisation techniques or the like.

In one embodiment the step of recovering the solvent drying solution is achieved by a pressure assisted osmosis technique.

The foregoing brief summary broadly describes the features and technical advantages of certain embodiments of the present invention. Further technical advantages will be described in the detailed description of the invention and examples that follows.

Novel features that are believed to be characteristic of the invention will be better understood from the detailed description of the invention when considered in connection with any accompanying figures and examples. However, the figures and examples provided herein are intended to help illustrate the invention or assist with developing an understanding of the invention, and are not intended to limit the invention's scope.

DETAILED DESCRIPTION OF THE INVENTION

Figure 1:
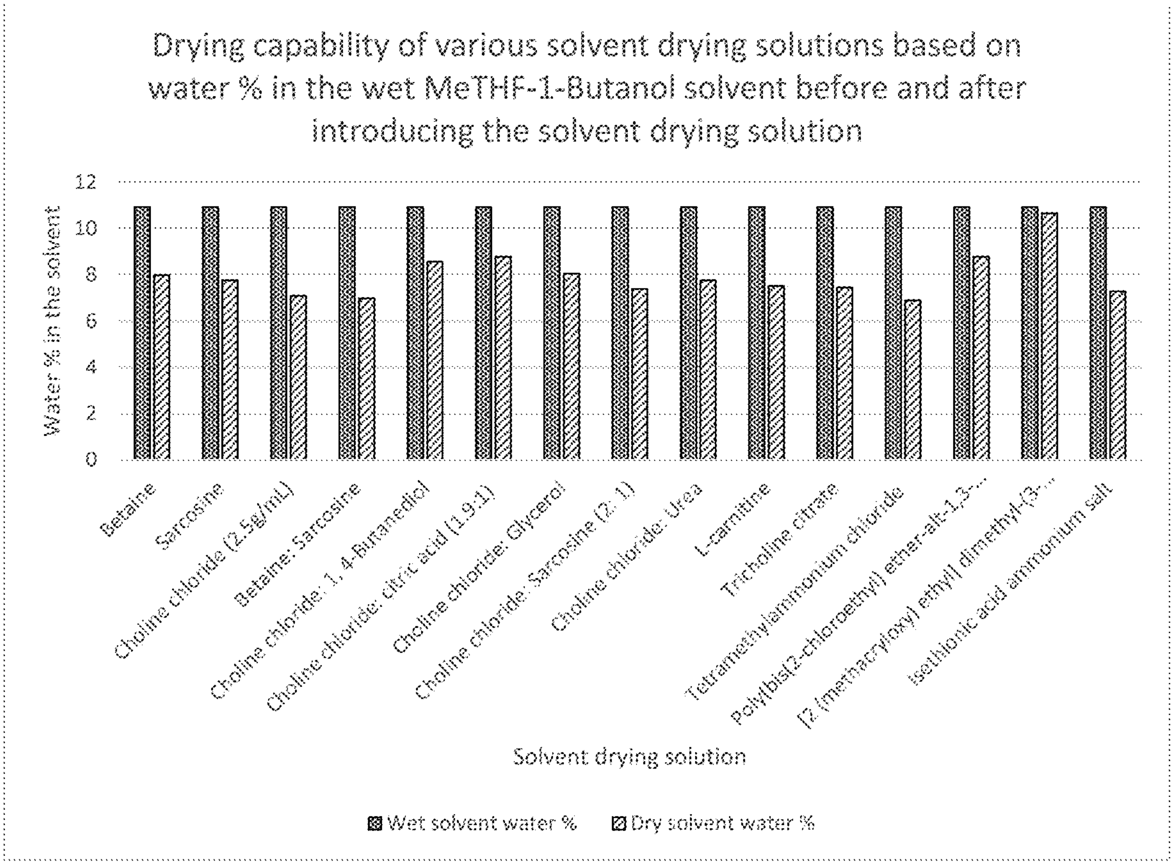
FIG. 1: shows the drying capacity of various solvent drying solutions based on water % in a wet solvent of MeTHF and 1-butanol before and after introducing the solvent drying solution.

The following description sets forth numerous exemplary configurations, parameters, and the like. It should be recognised, however, that such description is not intended as a limitation on the scope of the present invention but is instead provided as a description of exemplary embodiments.

Definitions

In each instance herein, in descriptions, embodiments, and examples of the present invention, the terms "comprising", "including", etc., are to be read expansively, without limitation. Thus, unless the context clearly requires otherwise, throughout the description and the claims, the words "comprise", "comprising", and the like are to be construed in an inclusive sense as to opposed to an exclusive sense, that is to say in the sense of "including but not limited to".

The term "about" or "approximately" usually means within 20%, more preferably within 10%, and most preferably still within 5% of a given value or range. Alternatively, the term "about" means within a log (i.e., an order of magnitude) preferably within a factor of two of a given value.

As used herein, the term "at least one $C_1$-$C_7$ alkyl amine or quaternary ammonium containing compound" means any compound that includes an —$NH_3$, —$NHR^3$ or —$NR^3R^4$ group wherein each $R^3$ and $R^4$ are selected from $C_1$-$C_7$ alkyl as defined below or a compound containing —$NH_4^+$ or —$N(R)_4^+$ where each R is independently selected from H, $C_1$-$C_3$ alkyl as defined below, such as betaine; carnitine, choline, each optionally with a counterion, such as carnitine chloride, choline chloride, choline iodide, choline bromide, tricholine citrate; tetraethylammonium chloride; tetramethylammonium chloride; acetyl choline chloride, (4-vinylbenzyl) trimethylammonium chloride, or a quaternary ammonium containing compound, such as [2(methacryloxyl) ethyl]dimethyl-(3-sulfopropyl) ammonium hydroxide; with the proviso that ammonium bicarbonate is excluded.

As used herein, the term "alkylsulfonic acid" includes any compound having a R—$S(O)_2OH$ functional group or a salt thereof, where R is a $C_1$-$C_7$ alkyl, wherein $C_1$-$C_7$ alkyl is as defined below.

As used herein, the term "$C_1$-$C_3$ alkyl" refers to a fully saturated hydrocarbon moiety. Representative examples of $C_1$-$C_3$alkyl include, but are not limited to, methyl, ethyl, n-propyl and iso-propyl.

As used herein, the term "$C_1$-$C_7$ alkyl" refers to a fully saturated branched or unbranched hydrocarbon moiety, which may be a straight or a branched chain of a particular range of 1-7 carbons. Preferably the alkyl comprises 1 to 7 carbon atoms, or 1 to 4 carbon atoms. Representative examples of $C_1$-$C_7$alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, and the like. For example, the expression $C_1$-$C_4$-alkyl includes, but is not limited to, methyl, ethyl, propyl, butyl, isopropyl, tert-butyl and isobutyl. In one embodiment the $C_1$-$C_7$ alkyl group may be substituted with one or more of the following groups:-halo, —OH, —CN, —$NO_2$, —C≡CH, —SH, —$C_1$-$C_7$ alkyl, —($C_1$-$C_7$ alkyl)-OH, —$NH_2$, —NH($C_1$-$C_7$ alkyl), —N($C_1$-$C_7$ alkyl)$_2$, —O ($C_1$-$C_7$alkyl), —C(O)—O(—$C_1$-$C_7$ alkyl), —C(O)OH; —C(O)—H, or —C(O)—($C_1$-$C_7$ alkyl).

The term "halo" as used herein refers to —F, —Cl, —Br or —I.

As used herein, the term "$C_3$-$C_9$ alkyl" refers to a fully saturated branched or unbranched hydrocarbon moiety, which may be a straight or a branched chain of a particular range of 3-9 carbons. Preferably the alkyl comprises 3 to 7 carbon atoms, or 3 to 6 carbon atoms. Representative examples of $C_3$-$C_9$alkyl include, but are not limited to n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, and the like.

The term "$C_4$-$C_9$ ether containing compound" as used herein is a 4-, 5-, 6-, 7-, 8-or 9-membered saturated, unbranched, branched, or cyclic ether. Representative unbranched $C_4$-$C_9$ ether groups include, but are not limited to, methoxyethane, 1-methoxypropane, 1-methoxybutane, 1-methoxypentane, 1-methoxyhexane, 1-methoxyheptane and 1-methoxyoctane, ethoxyethane, 1-ethoxypropane, 1-ethoxybutane, 1-ethoxypentane, 1-ethoxyhexane, 1-ethoxyheptane, 1-propoxypropane, 1-propoxybutane, 1-propoxypentane, 1-propoxyhexane, 1-butoxybutane, 1-butoxypentane, Representative branched $C_4$-$C_9$ ether groups include, but are not limited to: 2-methoxypropane, 2-ethoxypropane, 1-isopropoxypropane, 1-isopropoxybutane, 1-isopropoxypentane, 1-isopropoxyhexane, 2-methoxy-2-methylpropane, 2-ethoxy-2-methylpropane, 2-methyl-2-propoxypropane, 1-(tert-butoxy)butane, 1-(tert-butoxy)pentane, 2-(tert-butoxy)-2-methylpropane, 2-isopropoxy-2-methylpropane, 2-(tert-butoxy)butane, 1-(tert-butoxy)-2,2-dimethylpropane. Representative cyclic $C_4$-$C_9$ ether groups include, but are not limited to: oxetane, tetrahydrofuran, 2-methyltetrahydrofuran, 3-methyltetrahydrofuran, 2-ethyltetrahydrofuran, 3-ethyltetrahydrofuran, 2-methyltetrahydro-2H-pyran, 3-methyltetrahydro-2H-pyran, 4-methyltetrahydro-2H-pyran, 2,4-dimethyltetrahydro-2H-pyran, 2-ethyltetrahydro-2H-pyran, 3-ethyltetrahydro-2H-pyran, 4-ethyltetrahydro-2H-pyran, oxepane, oxocane, oxanane, 1,3 dioxolane, dioxane, 1,4-dioxepane, 1,5-dioxocane, 1,5-dioxanane. In one embodiment, the $C_4$-$C_9$ ether containing compound may be substituted with one or more —OH.

The term "$C_{4-}$ to $C_{9-}$ ketone or diketone" refers to a $C_{4-}$ to $C_{9-}$ membered straight chain, branched or cyclic compound containing one or two ketone functional group. Representative examples of a $C_{4-}$ to $C_{9-}$ membered ketone include, but are not limited to butanone, pentanone, hexanone, heptanone, octanone, nonanone, heptane-2,6-dione, acetonylacetone, cyclohexanone, 4-methylcyclohexanone, methylethylketone, 1,2 diektones such as 2,3-pentanedione.

The term "$C_4$-$C_9$ ester containing compound" as used herein is a 4-, 5-, 6-, 7-, 8-or 9-membered saturated, unbranched, branched, ester. Representative $C_4$-$C_9$ ester containing compounds as used herein include but are not limited to ethyl acetate, propylacetate, methyl propionate, ethyl propionate, propyl propionate, butyl propionate, butyl butyrate, isopentyl acetate, 3,3-dimethylbutyl acetate, 3,3-dimethylbutyl propionate, isopropyl propionate, tert-butyl propionate; ethyly propionate, methyl pivalate, ethyl pivalate.

The term "$C_4$-$C_9$ glycol ether" as used herein is a 4-, 5-, 6-, 7-, 8-or 9-membered saturated, unbranched, branched, or glycol ether which includes without limitation from propylene glycol methyl ether, dipropylene glycol methyl ethyl acetate, dipropylene glycol n-propyl ether, propylene glycol n-butyl ether, dipropylene glycol n-butyl ether, tripropylene glycol n-butyl ether, propylene glycol phenyl ether, propylene glycol diacetate. Preferably the glycol ether has a solubility of less than 30 wt % in water, more preferably, less than 20 wt % solubility in water.

The term "amine containing compound" as used herein is a primary, secondary or tertiary amine. Preferably the amine containing compound is a tertiary amine compound.

A solvent drying solution is provided to remove water from a solvent the solution comprising:

a) at least one $C_1$-$C_7$ alkyl amine or quaternary ammonium containing compound; or
b) at least one carboxylic acid containing compound or an alkylsulfonic acid; or
c) at least one straight chain or branched $C_3$-$C_9$ alkyl substituted by —OH; or
d) a combination of a) to c) thereof, in a water containing solvent comprising at least two or more components independently selected from any combination of integers i), ii), iii) or iv), where:

i) is a straight, branched or optionally substituted cyclic $C_4$-$C_9$ ether containing compound;
ii) is a straight chain or branched $C_3$-$C_9$ alkyl substituted by —OH;
iii) is a straight chain, branched or cyclic $C_4$-$C_9$ ketone or $C_4$-$C_9$ diketone; and
iv) is a straight chain or branched $C_3$-$C_9$ ester containing compound;

wherein at least one component of the water containing solvent is substantially immiscible with an aqueous solution of 1 molar sodium chloride at or above 20 degrees Celsius and at 1 atmosphere.

It is to be appreciated that a number of carboxylic acids containing compounds could be used in the solvent drying solution. It is envisaged that a combination of one or more carboxylic acid containing compounds could be utilised. In one embodiment the carboxylic acid containing compound is selected from one or more of the following:

a) a compound of Formula I,

Formula I

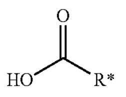

wherein R* is selected from, —$C_1$-$C_7$ alkyl-OH, —$C_1$-$C_7$ alkyl, —$C_1$-$C_7$ alkyl-$NH_2$, —$C_1$-$C_7$ alkyl-$NHR_3$ and —$C_1$-$C_7$ alkyl $NR_3R_4$, wherein each $R_3$ and $R_4$ are selected from —H, —OH, -halo, —$C_1$-$C_7$ alkyl, —$C_1$-$C_7$ alkyl-OH, —C(O)OH, —C(O)—H, or —C(O)—($C_1$-$C_7$ alkyl); and b) a polymer containing one or more carboxylic acid groups.

In one embodiment the water containing solvent comprises an amine containing compound as a substitute to one of integers i), ii), iii) and iv).

In one embodiment the solvent drying solution comprises at least one $C_1$-$C_7$ alkyl amine or quaternary ammonium containing compound, such as betaine, urea and choline chloride.

In one embodiment the solvent drying solution comprises at least one straight chain or branched $C_3$-$C_9$ alkyl substituted by —OH.

In one embodiment the at least one straight chain or branched $C_3$-$C_9$ alkyl substituted by —OH of the solvent drying solution includes at least two —OH substituents.

In one embodiment the at least one straight chain or branched $C_3$-$C_9$ alkyl substituted by —OH of the solvent drying solution is selected from 1,4 butanediol, glycerol or combinations thereof.

In one embodiment the $C_4$-$C_9$ ether containing compound is selected from one or more of 2-methyltetrahydrofuran, 3-methyltetrahydrofuran, 2-ethyltetrahydrofuran, 3-ethyltetrahydrofuran, dioxane, 1-ethoxypropane, and a $C_4$-$C_9$ glycol ether or combinations thereof.

In one embodiment the straight chain or branched $C_3$-$C_9$ alkyl substituted by —OH is selected from one or more of 1-butanol, 2, butanol and 1-pentanol or combinations thereof.

In one embodiment the $C_4$-$C_9$ glycol ether is selected from one or more of propylene glycol methyl ether, dipropylene glycol methyl ethyl actetate, dipropylene glycol n-propyl ether, propylene glycol n-butyl ether, dipropylene glycol n-butyl ether, tripropylene glycol n-butyl ether, propylene glycol phenyl ether, propylene glycol diacetate or combinations thereof.

In one embodiment the $C_4$-$C_9$ ketone or diketone is selected from one or more of acetonylacetone or 2-butanone.

It is to be appreciated that the molar ratios of two components in the solvent drying solution may be selected from about 1:99 or 99:1; or about 1:50 or 50:1; or about 1:10 or 10:1; or about 1:5 or 5:1; or about 1:3 or 3:1; or about 1:2 or 2:1; or about 1:1.

The disclosure also provides a method of recovering water from a solvent drying solution, the method including the steps of contacting the water containing solvent as defined above with:

a) at least one $C_1$-$C_7$ alkyl amine or quaternary ammonium containing compound and
b) at least one carboxylic acid containing compound, or an alkylsulfonic acid;
c) at least one at least one straight chain or branched $C_3$-$C_9$ alkyl substituted by —OH; or
d) a combination of a) to c) thereof, where upon contact the water is released from the water containing solvent to form an immiscible layer with the water depleted solvent.

It is to be appreciated that there are many processes that may include this step. One such process is a counter current process. Such a process involves the solvent drying solution being recycled in a counter current manner for use on progressively wetter solvents. Accordingly, in one embodiment the method defined herein may be used in a counter current process.

In one embodiment method includes the step of separating the recovered water from the immiscible water depleted solvent layer. Because the water forms an immiscible layer, it can be physically separated from the solvent layer.

In one embodiment the process includes the step of recovering the solvent. It is envisaged for example that the recovered solvent drying solution may be recycled for use in a further solvent drying process. Preferably, the process of recovering the solvent drying solution is a continuous recovery process.

In one embodiment the step of recovering the solvent drying solution is achieved by one or more of the following well known techniques, such as including membrane distillation, pervaporation, osmosis, pressure driven membrane processes, osmotically driven membrane processes, osmotically assisted pressure driven membrane processes, pressure assisted osmotically driven membrane processes, filtration, mechanical vapor recompression, evaporation based processes, water specific reactant, or crystallisation techniques or the like.

EXAMPLES

The examples described herein are provided for the purpose of illustrating specific embodiments of the invention and are not intended to limit the invention in any way. Persons of ordinary skill can utilise the disclosures and teachings herein to produce other embodiments and variations without undue experimentation. All such embodiments and variations are considered to be part of this invention.

Example 1—The Water Removal Capability of Various Solvent Drying Solutions

Various types of compounds with different types of functional group were tested as solvent drying solutions. These solutions included different types of functional groups such as zwitterions, quaternary ammonium containing compounds or alcohols. The water removal capability of the solvent drying solutions was determined by analytical methods and their performances were compared.

Solvent drying solutions were prepared using betaine (trimethyl glycine), choline chloride, sarcosine, 1,4-butanediol, urea and glycerol and combinations thereof as outlined in Table 1.

TABLE 1

List of solvent drying solutions along with their concentrations/mole ratios

| Solvent drying solution | Concentration (g/mL) | Mole ratio of component 1 to 2 | Molar Concentration (mol/L) |
|---|---|---|---|
| Betaine | 1.2 | | 5.12 |
| Sarcosine | 1.48 | | 8.1 |
| Choline chloride | 2.5 | | 3.67 |
| Betaine:Sarcosine | | 1.6:1 | 6.94 |
| Choline chloride:1,4-Butanediol | | 1:2 | 7.15 |
| Choline chloride:Glycerol | | 1:2 | 7.633 |
| Choline chloride:Urea | | 1:2 | 9.785 |
| Choline chloride:Sarcosine | | 2:1 | 5.86 |
| L-carnitine | 2.1 | | 4.94 |

TABLE 1-continued

List of solvent drying solutions along with their concentrations/mole ratios

| Solvent drying solution | Concentration (g/mL) | Mole ratio of component 1 to 2 | Molar Concentration (mol/L) |
|---|---|---|---|
| Tricholine citrate | 1.86 | | 1.52 |
| Acetyl choline chloride | 4 | | 1.76 |
| Tetramethylammonium chloride | 2 | | 6.29 |
| Tetraethylammonium chloride | 2 | | 4.16 |
| (Vinylbenzyl) tetramehtylammonium chloirde | 4 | | 4.7 |
| Poly(bis(2-chloroethyl) ether-alt-1,3-bis{3-(dimethylamino)propyl}urea | 1.63 | | Polymeric mixture |
| [2 (methacryloxy) ethyl] dimethyl-(3-sulfopropyl) ammonium hydroxide | 4 | | 3.25 |
| Isethionic acid ammonium salt | 2 | | 6 |

Solvent 1 2-Methyltetrahydrofuran (MeTHF) and 1-Butanol

The solvent mixture of 2-methyltetrahydrofuran (MeTHF) and 1-butanol combined at a molar ratio of 2:3 was also prepared.

Samples containing the solvent and the solvent drying solution were mixed in a vortex mixer for 30 seconds. After ensuring thorough mixing, these samples were centrifuged at 4000 rpm for 1 minute for any precipitated salts to settle at the bottom of the sample tubes.

Gas chromatography (GC) (Shimadzu Nexis GC-2030) was used to quantify the water % in the solvent post drying by the solvent drying solution.

A hydrated solvent of 2-methyltetrahydrofuran (MeTHF) and 1-butanol was prepared such that the water % was around 10% to create a wet solvent sample. Solvent drying solutions were added to the wet solvent sample and were mixed using the vortex mixer followed by centrifuging the sample for the emulsions to settle down. The ratio at which the solvent drying solution was added to the wet solvent was 1:20 by volume.

For this experiment, 5 mL of wet solvent was taken in centrifuge tubes and to each of these samples, solvent drying solutions were added. After mixing and centrifuging, 8 mL of solvent phase was pipetted out into GC vials for testing. The dry solvent samples were injected into the GC to quantify the water % accurately. The drying capacity for different solvent drying solutions were measured and plotted.

The list of solvent drying solutions contained both single component systems as well as multi-component systems. The following table 2 shows the various compounds and their concentrations selected to prepare the solvent drying solutions:

TABLE 2

The following table provides the drying capacity of the solvent drying solutions:

| Solvent drying solution | Starting water % | Water % after drying | Water removed |
|---|---|---|---|
| Betaine | 10.931 | 7.991 | 2.94 |
| Sarcosine | 10.931 | 7.77 | 3.16 |
| Choline chloride (2.5 g/ml) | 10.931 | 7.091 | 3.84 |
| Betaine:Sarcosine (1.6:1) | 10.931 | 6.982 | 3.949 |
| Choline chloride:1,4-Butanediol (1:2) | 10.931 | 8.575 | 2.36 |
| Choline chloride:Glycerol | 10.931 | 8.047 | 2.88 |
| Choline chloride:Sarcosine (1:2) | 10.931 | 6.982 | 3.95 |
| Choline chloride:Sarcosine (2:1) | 10.931 | 7.381 | 3.55 |
| Choline chloride:Urea | 10.931 | 7.769 | 3.16 |
| L-carnitine | 10.931 | 7.519 | 3.412 |
| Tricholine citrate | 10.931 | 7.458 | 3.473 |
| Tetramethylammonium chloride | 10.931 | 6.896 | 4.035 |
| Poly[bis(2-chloroethyl) ether-alt-1,3-bis[3-(dimethylamino)propyl]urea] quaternized solution | 10.931 | 8.784 | 2.147 |
| [2(methacryloxy)ethyl]dimethyl-(3-sulfopropyl)ammonium hydroxide | 10.931 | 10.165 | 0.766 |
| Isoethionic acid ammonium salt | 10.931 | 7.281 | 3.65 |

The results tabulated in Table 2 are also shown in FIG. 1.

Solvent 2 Ethyl Acetate and 2-Butanone

A solvent mixture of ethyl acetate and 2-butanone combined at a molar ratio of 1:4 was also prepared.

Samples containing the solvent and the solvent drying solution were mixed in a vortex mixer for 30 seconds. After ensuring thorough mixing, these samples were centrifuged at 4000 rpm for 1 minute for any precipitated salts to settle at the bottom of the sample tubes.

Gas chromatography (GC) (Shimadzu Nexis GC-2030) was used to quantify the water % in the solvent post drying by the solvent drying solution.

A hydrated solvent of ethyl acetate and 2-butanone was prepared such that the water % was around 6% to create a wet solvent sample. Solvent drying solutions were added to the wet solvent sample and were mixed using the vortex mixer followed by centrifuging the sample for the emulsions to settle down. The ratio at which the solvent drying solution was added to the wet solvent was 1:20 by volume.

For this experiment, 5 mL of wet solvent was taken in centrifuge tubes and to each of these samples, solvent drying solutions were added. After mixing and centrifuging, 1 mL of solvent phase was pipetted out into GC vials for testing. The dry solvent samples were injected into the GC to quantify the water % accurately. The drying capacity for different solvent drying solutions were measured and plotted.

The list of solvent drying solutions contained both single component systems as well as multi-component systems. The following table 3 shows the various compounds and their concentrations selected to prepare the solvent drying solutions:

TABLE 3

The following table provides the drying capacity of the solvent drying solutions:

| Solvent drying solution | Starting water % | Water % after drying | Water removed |
|---|---|---|---|
| Betaine | 6.218 | 3.846 | 2.372 |
| Sarcosine | 6.218 | 3.607 | 2.611 |
| Choline chloride (2.5 g/ml) | 6.218 | 3.143 | 3.075 |
| Betaine:Sarcosine | 6.218 | 3.367 | 2.851 |
| Choline chloride:1,4-Butanediol (1:2) | 6.218 | 4.472 | 1.746 |
| Choline chloride:Glycerol | 6.218 | 3.41 | 2.808 |
| Choline chloride:Sarcosine (2:1) | 6.218 | 3.054 | 3.164 |
| Choline chloride:Urea | 6.218 | 3.616 | 2.602 |
| L-carnitine | 6.218 | 3.527 | 2.691 |
| Tricholine citrate | 6.218 | 3.645 | 2.573 |
| Acetyl choline chloride | 6.218 | 3.118 | 3.100 |
| Tetramethylammonium chloride | 6.218 | 2.959 | 3.259 |
| Tetraethylammonium chloride | 6.218 | 3.407 | 2.811 |
| (vinylbenzyl)tetramethylammonium chloride | 6.218 | 4.385 | 1.833 |
| Poly[bis(2-chloroethyl) ether-alt-1,3-bis[3-(dimethylamino)propyl]urea] quaternized solution | 6.218 | 3.914 | 2.304 |
| [2(methacryloxy)ethyl]dimethyl-(3-sulfopropyl)ammonium hydroxide | 6.218 | 5.09 | 1.128 |
| Isoethionic acid ammonium salt | 6.218 | 3.435 | 2.783 |

Figure 2:
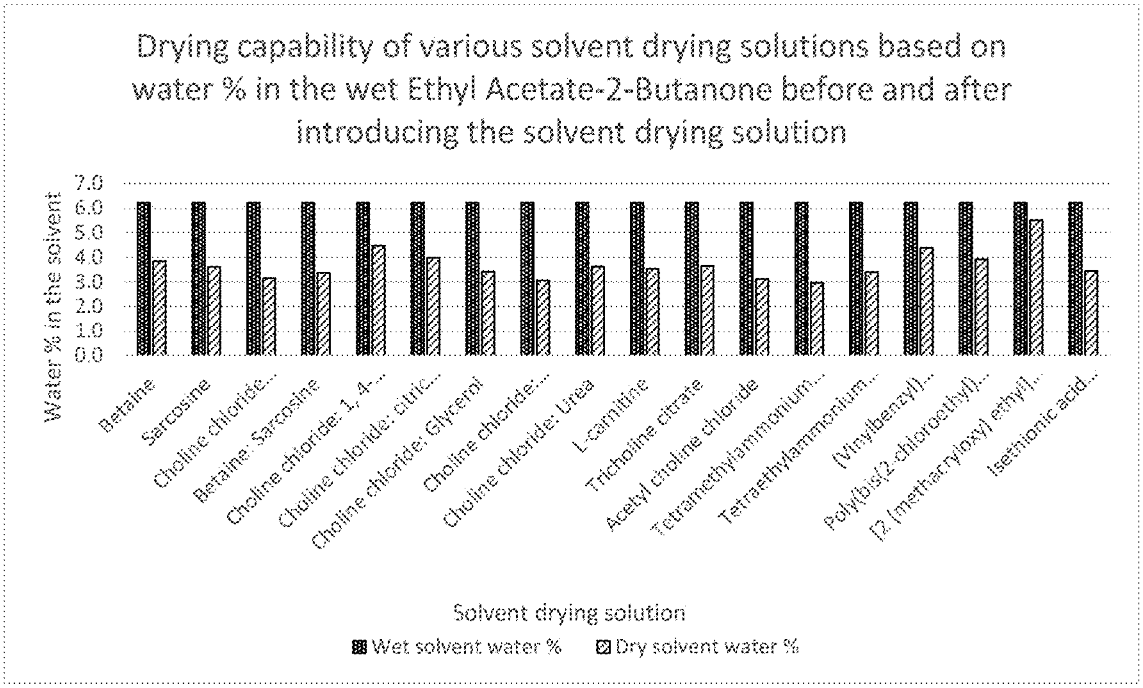
FIG. 2 shows the drying capacity of various solvent drying solutions based on water % in a wet solvent of ethyl acetate and 2-butanone before and after introducing the solvent drying solution.

The results tabulated in Table 3 are also shown in FIG. 2.

Solvent 3 Ethyl Acetate and 1-Butanol

A solvent mixture of ethyl acetate and 1-butanol combined at a molar ratio of 2:3 was also prepared.

Samples containing the solvent and the solvent drying solution were mixed in a vortex mixer for 30 seconds. After ensuring thorough mixing, these samples were centrifuged at 4000 rpm for 1 minute for any precipitated salts to settle at the bottom of the sample tubes.

Gas chromatography (GC) (Shimadzu Nexis GC-2030) was used to quantify the water % in the solvent post drying by the solvent drying solution.

A hydrated solvent of ethyl acetate and 1-butanol was prepared such that the water % was around 11% to create a wet solvent sample. Solvent drying solutions were added to the wet solvent sample and were mixed using the vortex mixer followed by centrifuging the sample for the emulsions to settle down. The ratio at which the solvent drying solution was added to the wet solvent was 1:20 by volume.

For this experiment, 5 mL of wet solvent was taken in centrifuge tubes and to each of these samples, solvent drying solutions were added. After mixing and centrifuging, 1 mL of solvent phase was pipetted out into GC vials for testing. The dry solvent samples were injected into the GC to quantify the water % accurately. The drying capacity for different solvent drying solutions were measured and plotted.

The list of solvent drying solutions contained both single component systems as well as multi-component systems. The following table 4 shows the various compounds and their concentrations selected to prepare the solvent drying solutions:

TABLE 4

| The following table provides the drying capacity of the solvent drying solutions: | | | |
|---|---|---|---|
| | 10.90% Wet Abs Ethyl Acetate-1-Butanol | | |
| Solvent drying solution | Starting water % | Water % after drying | Water removed |
| Betaine | 10.90 | 8.52 | 2.38 |
| Sarcosine | 10.90 | 7.92 | 2.99 |
| Choline chloride | 10.90 | 8.43 | 2.47 |
| Choline chloride (2.5 g/mL) | 10.90 | 7.55 | 3.36 |
| Betaine:Sarcosine (1.6:1) | 10.90 | 7.75 | 3.16 |
| Choline chloride:1,4-Butanediol | 10.90 | 8.77 | 2.13 |
| Choline chloride:Glycerol | 10.90 | 8.96 | 1.95 |
| Choline chloride:Sarcosine (2:1) | 10.90 | 7.68 | 3.22 |
| Choline chloride:Urea | 10.90 | 8.75 | 2.16 |
| L-carnitine | 10.90 | 7.60 | 3.30 |
| Tricholine citrate | 10.90 | 7.56 | 3.34 |
| Tetramethylammonium chloride | 10.90 | 7.36 | 3.55 |
| Poly(bis(2-chloroethyl) ether-alt-1,3-bis{3-(dimethylamino)propyl}urea | 10.90 | 9.16 | 1.74 |
| [2 (methacryloxy) ethyl] dimethyl-(3-sulfopropyl) ammonium hydroxide | 10.90 | 10.60 | 0.31 |
| Isethionic acid ammonium salt | 10.90 | 7.57 | 3.33 |

Figure 3:
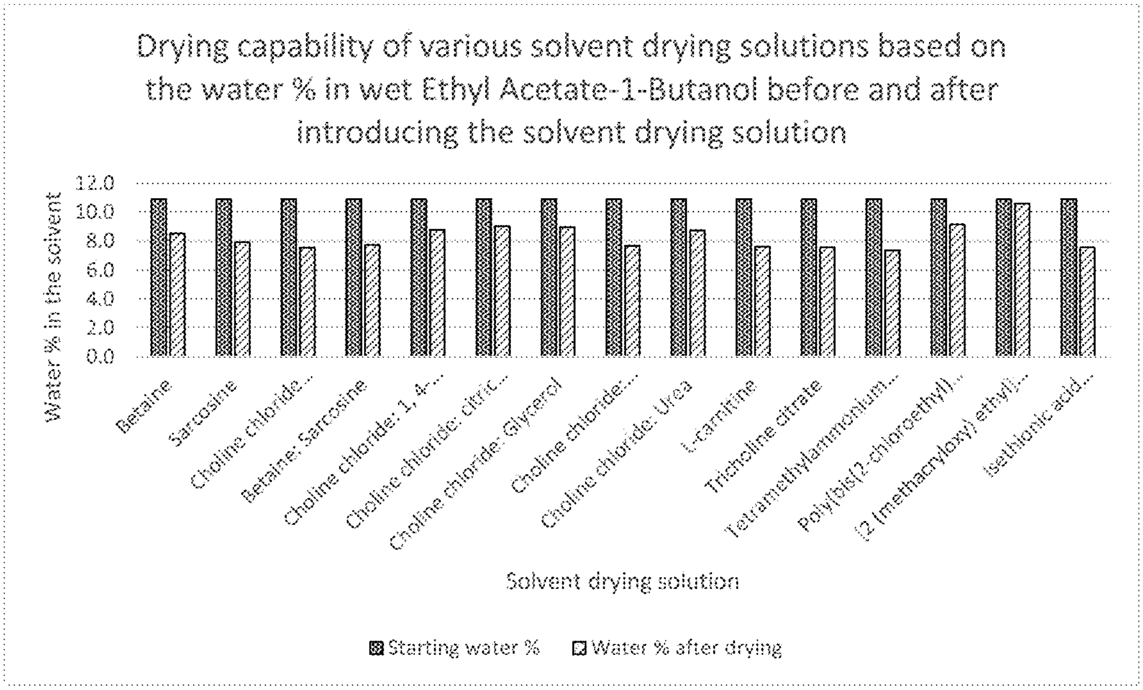
FIG. 3 shows the drying capability of various solvent drying solutions based on water % in a wet solvent of ethyl acetate and 1-butanol before and after introducing the solvent drying solution.

The results tabulated in Table 4 are also shown in FIG. 3.

Figure 4:
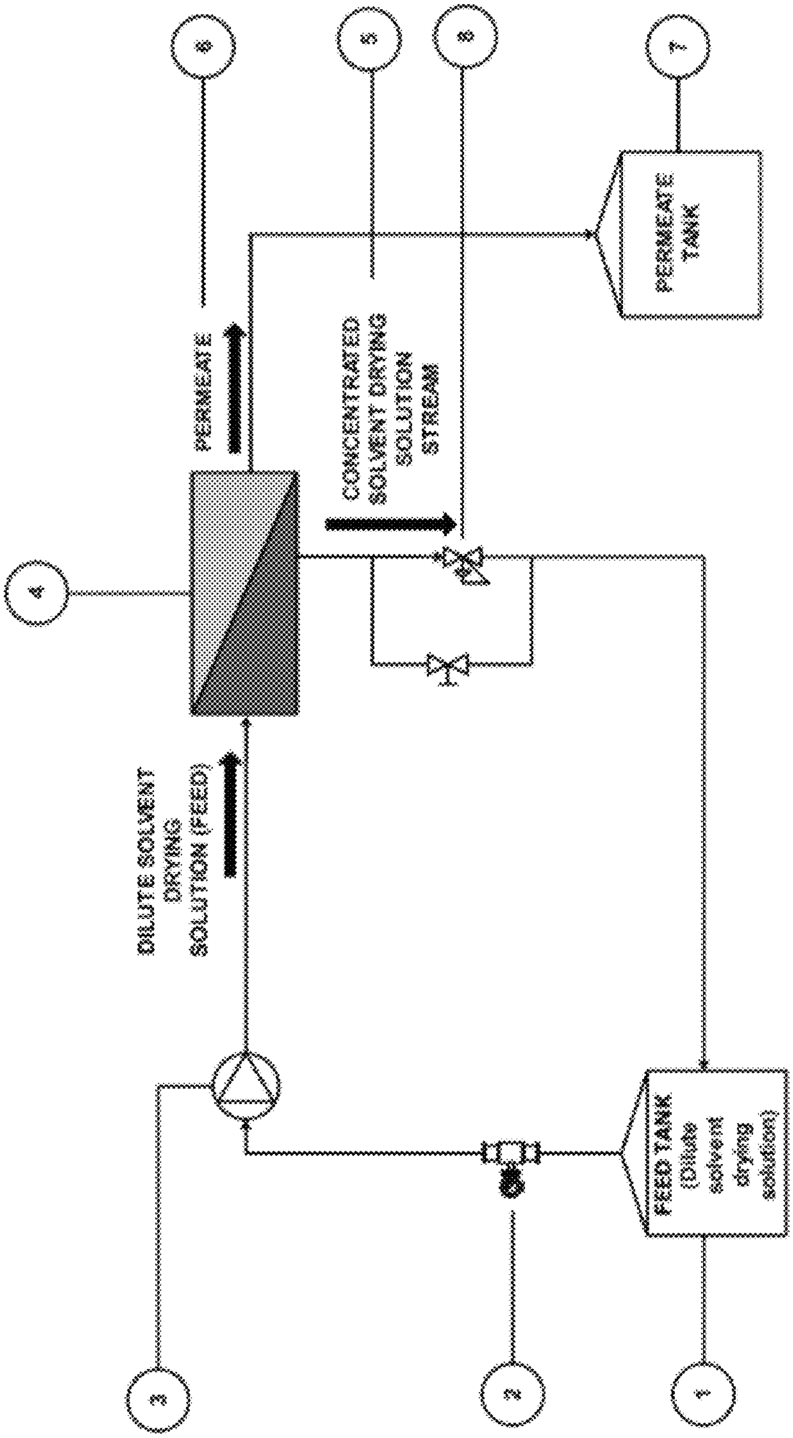
FIG. 4 shows a process diagram for a continuous process system for recovering a solvent drying solution.
Figure 5:
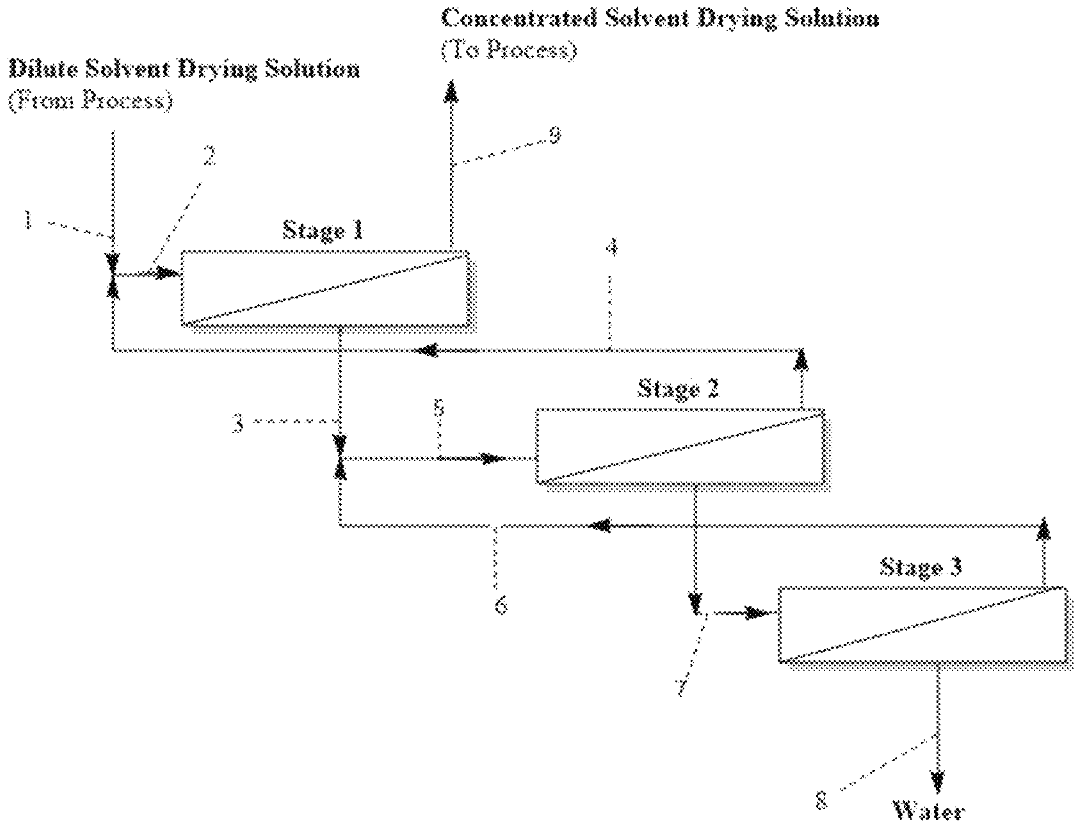
FIG. 5 shows a process diagram for a multistage solvent drying recovery process.

The results shown in Tables 2-4 (and FIG. 1 to 3 in graph format) show that the solvent drying solutions are effective at removing a significant proportion of water from the wet solvent solution. It is a to be appreciated that a continuous process for recovering a solvent drying solution could be possible. A process diagram of such a continuous process is shown schematically in FIG. 4. It is also to be appreciated that multiple passages or multistage regeneration of the wet solvent by a solvent drying solution will incrementally remove more water with very limited energy requirements and such a process is shown in FIG. 4. In FIG. 4, a possible pressure driven membrane process diagram is shown where diffusion based membranes, such as, without limitation, nanofiltration membranes, reverse osmosis membranes, molecular weight cut-off or seawater membranes may be utilised at each of the recovery stages, Stage 1, Stage 2 and Stage 3. It is to be appreciated that different membranes may be employed at each stage depending on the characteristics of the feed stream(s). It is to be further appreciated that the pressure at which the process will be run will also depend on the characteristics of the feed stream(s). A dilute solvent drying solution or wet solvent solution feed stream (1) at a concentration of around 60% (by volume) and at a rate of up to 150 $m^3$/hour will be fed into a mixed feed stream (2) that will then be fed into the first solvent drying stage, Stage 1. The mixed feed stream (2) combines the feed stream (1) with a feed stream (4) from the second solvent drying Stage 2. The mixed feed stream (2) will be fed at up to 175 $m^3$/hour at a concentration of about 59% (by vol) of the solvent drying solution in water. In Stage 1 the dilute solvent drying solution comes into contact with a solvent drying solution as described herein to remove a proportion of the water from the feed stream (2) and to form a concentrated solvent drying solution (9) which is anticipated to be at a concentration of about 90% by volume and at an anticipated flow rate of about 100 $m^3$/hour. The diluted solvent drying solution mixture recovered from Stage 1 will be fed as a feed stream (3) at an anticipated concentration of about 30% by volume solvent drying solution and at a flow rate of about 75 $m^3$/hour into mixed feed stream (5). Mixed feed stream (5) will comprise a mix of feed stream (3) and a feed stream (6) (from the third solvent drying Stage 3). It is anticipated the feed stream (5) will be fed into the second solvent drying stage, Stage 2, at a flow rate of about 100 $m^3$/hour and at a concentration of about 32% by volume solvent drying solution. A concentrated solvent drying feed stream (4) from Stage 2 will be fed back into freestream (2) at a flow rate of about 25 $m^3$/hour and at a concentration of about 56% solvent drying solution. A diluted solvent drying solution feed stream (7) from Stage 2 will be fed into the third solvent drying Stage 3. The feed stream (7) is anticipated to have a concentration of about 10% by volume of solvent drying solution. The feed stream (7) will be fed at an anticipated rate of about 75 m3 per hour into the third solvent drying stage, Stage 3. A feed stream (6) of a concentrated solvent drying solution (about 35%) will be recovered from Stage 3 and circulated back into mixed feed stream (5), which is fed into solvent drying Stage 2. A feedstream (8) of water will be collected from Stage 3 at a flow rate anticipated to be about 50 $m^3$/hour.

A further study was conducted looking at the use of carnitine, having an IUPAC name 3-Hydroxy-4-(trimethyl-azaniumyl)butanoate (a quaternary ammonium containing compound) as a solvent drying solution at various wetness. A hydrated solvent of 2-methyltetrahydrofuran (MeTHF) and 1-butanol was prepared such that the water % was varied (3.8%, 5.9% and 8% wet) to create a range of wet solvent samples. A solvent drying solution comprising 2.1 g/ml was added to the wet solvent samples and were mixed using the vortex mixer followed by centrifuging the sample for the emulsions to settle down. The ratio at which the solvent drying solution was added to the wet solvent was 1:20 by volume.

For this experiment, 5 mL of wet solvent was taken in centrifuge tubes and to each of the wet samples, the solvent drying solution comprising carnitine was added. After mixing and centrifuging, 1 mL of solvent phase was pipetted out into GC vials for testing. The dry solvent samples were injected into the GC to quantify the water % accurately. The drying capacity for different solvent drying solutions were measured and are tabulated below in Table 5.

TABLE 5

| Solvent Drying Solution | Concentration | 2-(MeTHF) and 1-butanol wetness of 3.8% after drying | 2-(MeTHF) and 1-butanol wetness of 5.9% after drying | 2-(MeTHF) and 1-butanol wetness of 8% after drying |
|---|---|---|---|---|
| Carnitine | 2.1 gm/ml | 3.416 | 4.804 | 5.938 |

Counter Current Example

Figure 6:
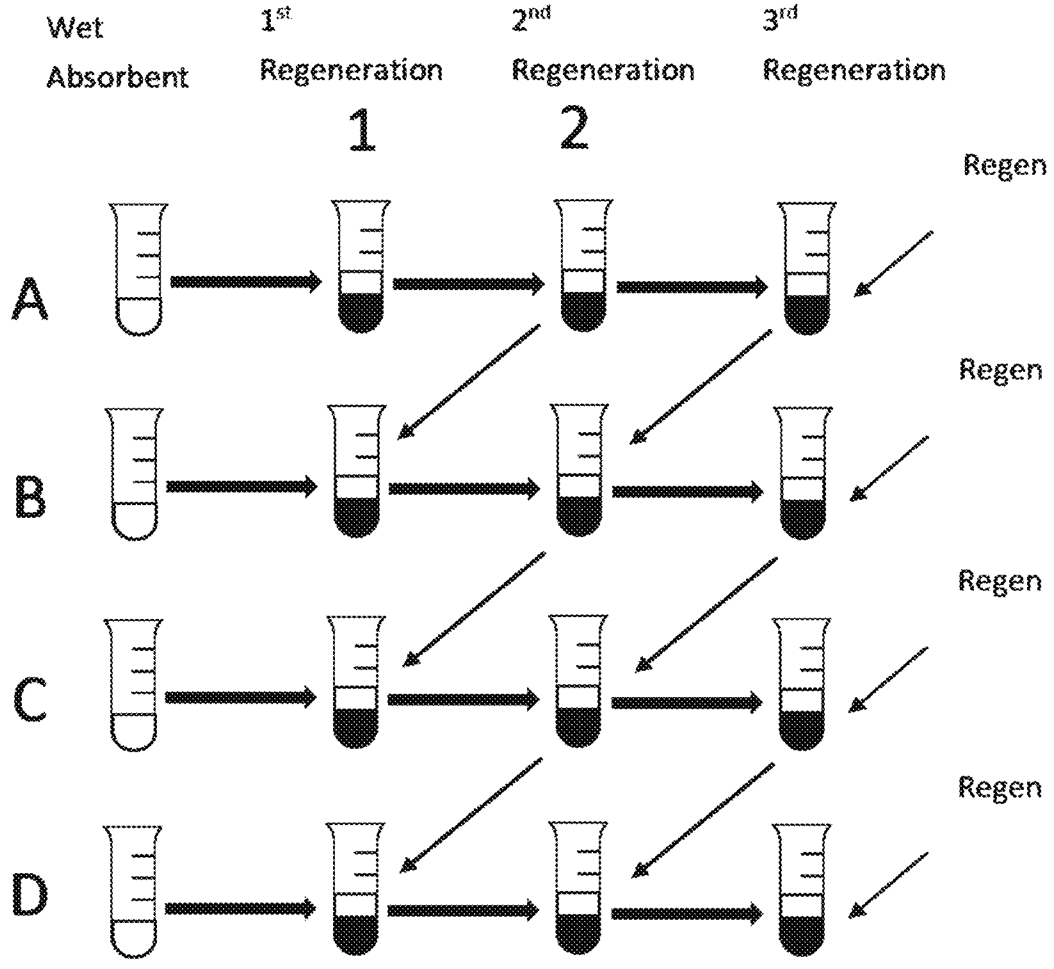
FIG. 6 shows schematically a three-stage counter current regeneration process.
Figure 7:
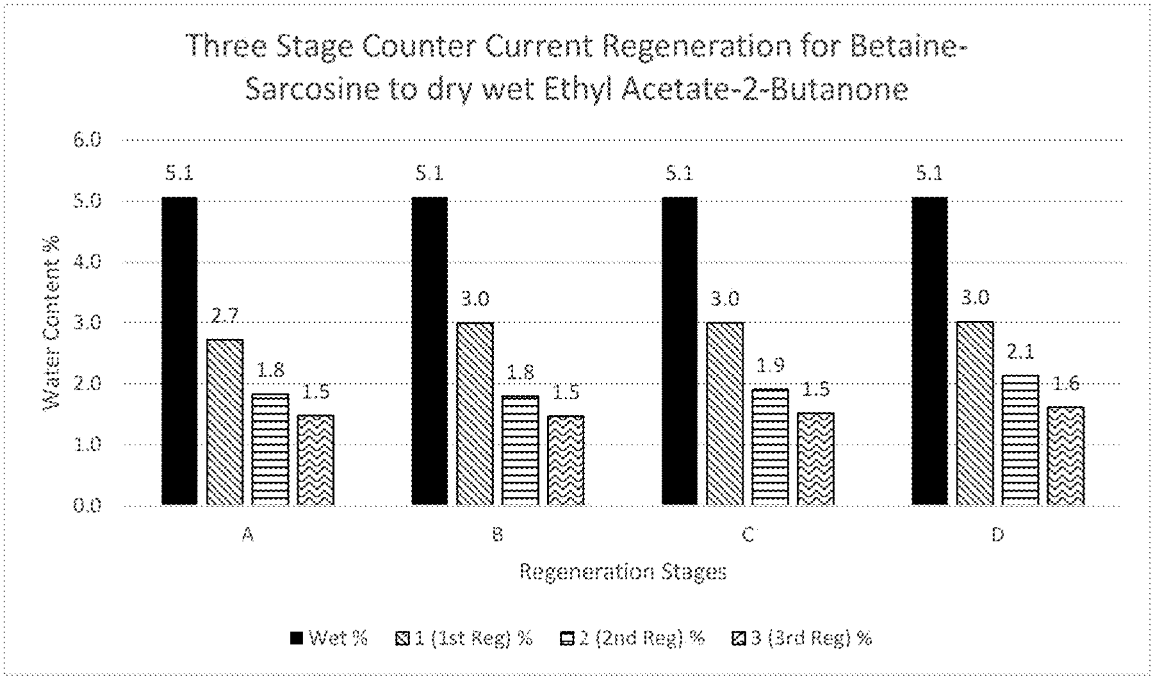
FIG. 7 shows the results of a three-stage counter current regeneration process using betaine sarcosine to dry the solvent mix of ethyl acetate and 2-butanone.
Figure 8:
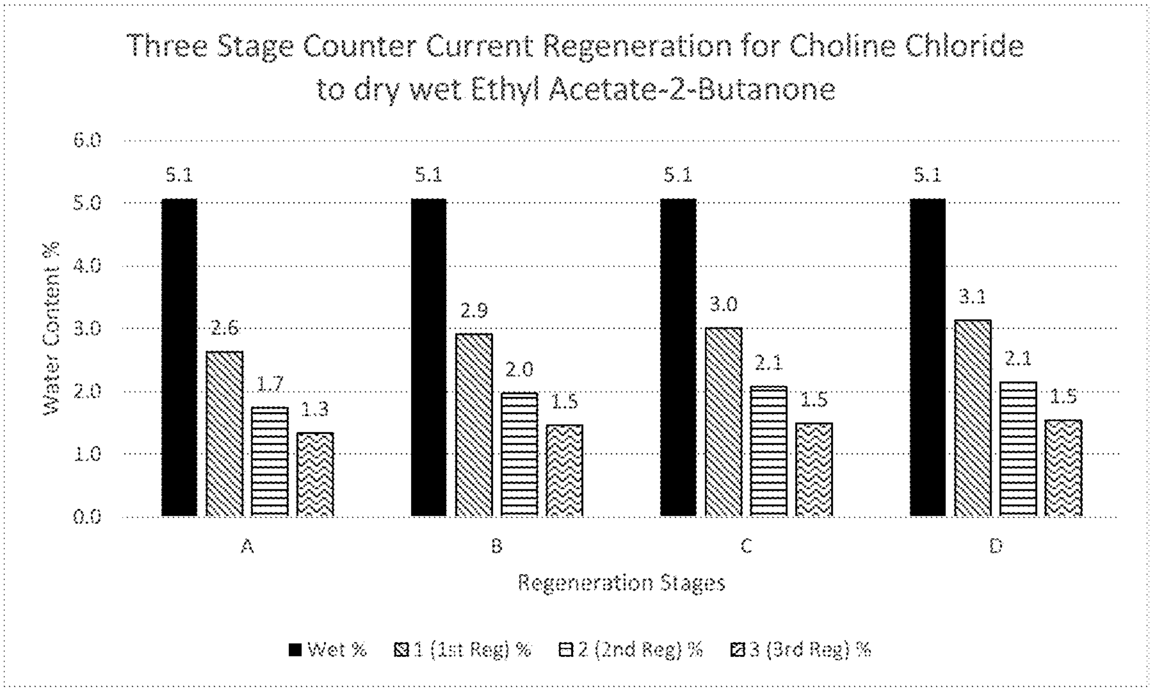
FIG. 8 shows the results of a three-stage counter current regeneration process using choline chloride to dry the solvent mix of ethyl acetate and 2-butanone.
Figure 9:
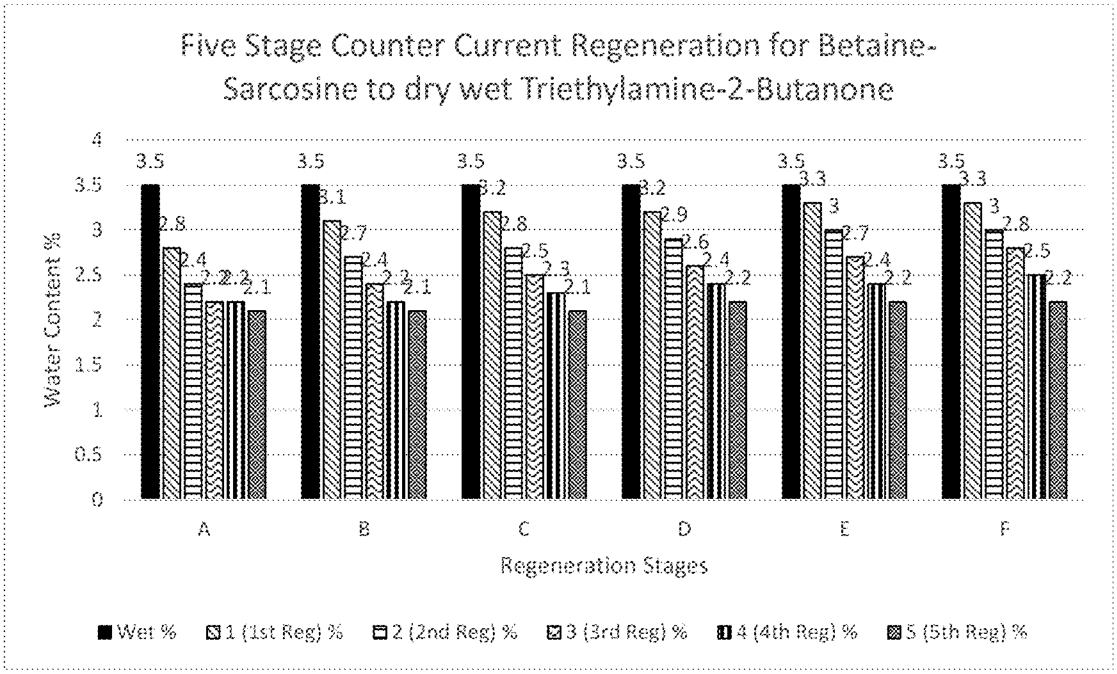
FIG. 9 shows the results of a five-stage counter current regeneration process using betaine-sarcosine to dry a solvent mix of triethylamine and 2-butanone.
Figure 10:
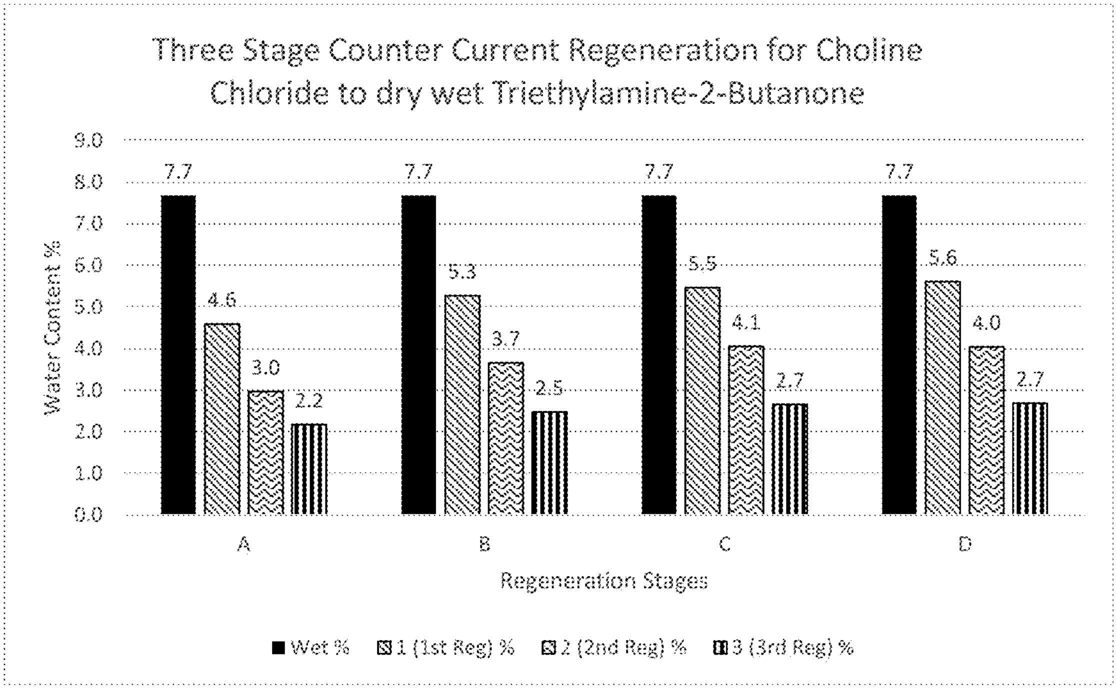
FIG. 10 shows the results of a three-stage counter current regeneration process using choline chloride to dry a solvent mix of triethylamine and 2-butanone.

The purpose of using counter current regeneration with a solvent drying solution is to reduce use of reverse osmosis to lower the overall energy used by the system. With reference to FIG. 6, a counter current process is shown. A wet solvent mixture (Wet Absorbent in FIG. 6) is prepared in which a brine is added to the solvent mixture at the intended ratio and mixed (Vortex for 30 seconds and centrifuge for 1 min at 4000 RPM). For the initial experiment A (shown in FIG. 6), multiple regeneration steps are undertaken. The dilute solvent drying solution (Regen) from the $2^{nd}$ Regen step is re-used for the $1^{st}$ regeneration step of the next stage (B). The $3^{rd}$ regeneration step always uses pure solvent drying solution (Regen). The now dilute Regenerant from the $3^{rd}$ regeneration is re-used for the $2^{nd}$ Regeneration of the next stage (B). This continues for as many stages as is necessary. At each stage the solvent drying solution (Regen) is added to the wet solvent mixture at a volumetric ratio of 1:20. The regeneration stages can be increased as well as the counter current stages depending on the intended wetness of the wet solvent mixture (Absorbent). FIG. 6 shows a three-stage counter current regeneration. If more stages were trialled than the amount of experiment stages needed to determine the full outcome of the counter current series Regeneration is one stage more than the Regeneration stages (e.g. Four stage Regeneration would require to be performed up until the E stage).

With reference to FIGS. 7 to 10, the results of various multiple stage counter current regeneration series with different wet solvent mixtures and different solvent drying solutions, as outlined in Table 6, are presented graphically. It can be seen that with successive regenerations steps the water content in the solvent mixture decreases. This shows that the solvent drying solution is removing water from the wet solvent mixture.

TABLE 6

| Solvent component molar ratio | | |
|---|---|---|
| Wet solvent mixture | Molar ratio of components | |
| Ethyl Acetate-2-Butanone | 1:4 | |
| Triethylamine-2-Butanone | 1:2 | |
| Water drying solvent concentration | | |
| Water drying solvent | Molar ratio of components | Molar concentration (mol/L) |
| Betaine-Sarcosine | 1.6:1 | 6.94 |
| Choline chloride | — | 3.67 |

The present invention and its embodiments have been described in detail. However, the scope of the present invention is not intended to be limited to the particular embodiments of any process, manufacture, composition of matter, compounds, means, methods, and/or steps described in the specification. Various modifications, substitutions, and variations can be made to the disclosed material without departing from the spirit and/or essential characteristics of the present invention. Accordingly, one of ordinary skill in the art will readily appreciate from the disclosure that later modifications, substitutions, and/or variations performing substantially the same function or achieving substantially the same result as embodiments described herein may be utilized according to such related embodiments of the present invention. Thus, the following claims are intended to encompass within their scope modifications, substitutions, and variations to combinations, kits, compounds, means, methods, and/or steps disclosed herein.

The invention claimed is:

1. A solvent drying solution, the solution comprising:

a) at least one $C_1$-$C_7$ alkyl amine or ammonium quaternary containing compound; or b) at least one carboxylic acid containing compound or an alkylsulfonic acid; or c) at least one straight chain or branched $C_3$-$C_9$ alkyl substituted by —OH; or d) a combination of a) to c) thereof, in a water-containing solvent comprising two or more components independently selected from any combination of integers i), ii), iii) and iv), where:

i) is a straight, branched or optionally substituted cyclic $C_4$-$C_9$ ether containing compound;

ii) is a straight chain or branched $C_3$-$C_9$ alkyl substituted by —OH;

iii) is a straight chain, branched or cyclic $C_4$-$C_9$ ketone or $C_4$-$C_9$ diketone; and iv) is a straight chain or branched $C_3$-$C_9$ ester containing compound;

wherein at least one component of the water containing solvent is substantially immiscible with an aqueous solution of 1 molar sodium chloride at or above 20 degrees Celsius and at 1 atmosphere.

2. The solvent drying solution of claim 1, comprising at least one carboxylic acid containing compound and wherein each of the carboxylic acid containing compounds are selected from one or more of the following:

a) a compound of Formula I,

Formula I

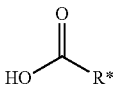

wherein R* is selected from, —$C_1$-$C_7$ alkyl-OH, —$C_1$-$C_7$ alkyl, —$C_1$-$C_7$ alkyl-$NH_2$, —$C_1$-$C_7$ alkyl-$NHR_3$ and —$C_1$-$C_7$ alkyl $NR_3R_4$, wherein each $R_3$ and $R_4$ are selected from —H, —OH, -halo, —$C_1$-$C_7$ alkyl, —$C_1$-$C_7$ alkyl-OH, —C(O) OH, —C(O)—H, or —C(O)—($C_1$-$C_7$ alkyl); and b) a polymer containing one or more carboxylic acid groups.

3. The solvent drying solution of claim 1, comprising at least one $C_1$-$C_7$ alkyl amine or quaternary ammonium containing compound.

4. The solvent drying solution of claim 3, wherein the at least one $C_1$-$C_7$ alkyl amine or quaternary ammonium containing compound of the solvent drying solution is selected from betaine, carnitine, urea, choline, or a combination thereof, each optionally with a counterion.

5. The solvent drying solution of claim 1 wherein the solvent drying solution comprises at least one straight chain or branched $C_3$-$C_9$ alkyl substituted by —OH.

6. The solvent drying solution of claim 5, wherein the at least one straight chain or branched $C_3$-$C_9$ alkyl substituted by —OH of the solvent drying solution includes at least two —OH substituents.

7. The solvent drying solution of claim 6, wherein the at least one straight chain or branched $C_3$-$C_9$ alkyl substituted by —OH of the solvent drying solution is selected from 1,4-butanediol, glycerol, or a combination thereof.

8. The solvent drying solution of claim 1 comprising at least one carboxylic acid containing compound.

9. The solvent drying solution of claim 1 wherein the water containing solvent comprises an amine containing compound as a substitute to one of integers i), ii), iii) and iv).

10. The solvent drying solution of claim 9, wherein the amine is a secondary or tertiary amine.

11. The solvent drying solution of claim 9, wherein the water-containing solvent comprises triethylamine and 2-butanone.

12. The solvent drying solution of claim 1, wherein the solvent drying solution comprises:
(a) betaine;
(b) choline chloride;
(c) sarcosine;
(d) a combination of betaine and sarcosine;
(e) a combination of choline chloride and 1,4-butanediol;
(f) a combination of choline chloride and glycerol;
(g) a combination of choline chloride and sarcosine; or
(h) a combination of choline chloride and urea.

13. The solvent drying solution of claim 12, comprising a combination of choline chloride and 1,4-butanediol and wherein the molar ratio of choline chloride to 1,4-butanediol is about 1:2.

14. The solvent drying solution of claim 12, comprising a combination of choline chloride and glycerol and wherein the molar ratio of choline chloride to glycerol is about 1:2.

15. The solvent drying solution of claim 12, comprising a combination of choline chloride and sarcosine and wherein the molar ratio of choline chloride to sarcosine is about 1:2.

16. The solvent drying solution of claim 12, comprising a combination of choline chloride and urea and wherein the molar ratio of choline chloride to urea is about 1:2.

17. The solvent drying solution of claim 1, wherein the water containing solvent comprises;
(a) a $C_4$-$C_9$ ether containing compound selected from: 2-methyltetrahydrofuran, 3-methyltetrahydrofuran, 2-ethyltetrahydrofuran, 3-ethyltetrahydrofuran, dioxane, 1-ethoxypropane, a $C_4$-$C_9$ glycol ether, or combinations thereof;
(b) a straight chain or branched $C_3$-$C_9$ alkyl substituted by —OH selected from: 1-butanol, 2-butanol, 1-pentanol, or combinations thereof;
(c) a $C_4$-$C_9$ glycol ether selected from propylene glycol methyl ether, dipropylene glycol methyl ethyl acetate, dipropylene glycol n-propyl ether, propylene glycol n-butyl ether, dipropylene glycol n-butyl ether, tripropylene glycol n-butyl ether, propylene glycol phenyl ether, propylene glycol diacetate, or combinations thereof;
(d) a $C_4$-$C_9$ ketone or diketone selected from acetonylacetone or 2-butanone;
(e) a $C_3$-$C_9$ ester selected from methyl acetate or ethyl acetate;
(f) a combination of 2-methyltetrahydrofuran and acetonylacetone;
(g) a combination of 2-methyltetrahydrofuran and 1-butanol;
(h) a combination of 2-methyltetrahydrofuran and 1-pentanol;
(i) a combination of ethyl acetate and 2-butanone;
(j) a combination of ethyl acetate and 2-methyltetrahydrofuran;
(k) a combination of ethyl acetate and 1-butanol; or
(l) a combination of ethyl acetate and acetonylacetone.

18. A method of recovering water from a solvent drying solution, the method including the steps of contacting the water-containing solvent of claim 1 with:
a) at least one $C_1$-$C_7$ alkyl amine or quaternary ammonium containing compound; or
b) at least one carboxylic acid containing compound, or an alkylsulfonic acid; or
c) at least one at least one straight chain or branched $C_3$-$C_9$ alkyl substituted by —OH; or
d) a combination of a) and b), a) and c), b) and c), or a), b), and c),
where upon contact the water is released from the water containing solvent to form an aqueous layer and an immiscible water depleted solvent layer.

19. The method of claim 18, wherein the method is included in a counter current process.

20. The method of claim 18, wherein the method includes the step of separating the released water from the immiscible water depleted solvent layer.

21. The method of claim 18, further including the step of recovering the solvent drying solution.

22. The method of claim 21 wherein the recovered solvent drying solution is recycled for use in a further method of recovering water.

23. The method of claim 22, wherein the step of recovering the solvent drying solution is a continuous recovery process.

24. The method of claim 23, wherein the step of recovering the solvent drying solution is achieved by one or more of the following; membrane distillation, pervaporation, osmosis, pressure driven membrane process, osmotically driven membrane processes, pressure assisted osmosis, osmotically assisted pressure driven membrane processes, pressure assisted osmotically driven membrane processes, filtration, mechanical vapor recompression, evaporation based processes, water specific reactant, or crystallisation.

* * * * *